United States Patent [19]

Renoe et al.

[11] Patent Number: 5,420,039
[45] Date of Patent: * May 30, 1995

[54] CONTROL OF CONTINUOUS MICROWAVE DIGESTION PROCESS

[75] Inventors: Brian W. Renoe, Matthews; Edward E. King; Dale A. Yurkovich, both of Charlotte, all of N.C.

[73] Assignee: CEM Corporation, Matthews, N.C.

[*] Notice: The portion of the term of this patent subsequent to Jun. 1, 2010 has been disclaimed.

[21] Appl. No.: 999,295

[22] Filed: Dec. 31, 1992

[51] Int. Cl.[6] .............................................. G01N 35/08
[52] U.S. Cl. ...................................... 436/52; 436/175; 422/21; 422/81; 422/186; 219/679; 219/693; 204/157.43; 204/158.2; 204/302; 204/308; 361/327
[58] Field of Search ........................... 422/21, 81, 186; 436/52, 175, 177; 219/10.55 R, 10.55 M; 204/158.2, 157.43, 302, 308; 361/301, 327, 328, 329

[56] References Cited

U.S. PATENT DOCUMENTS

| | | | |
|---|---|---|---|
| 3,912,452 | 10/1975 | Sodickson et al. | 422/81 X |
| 4,266,425 | 5/1981 | Allport | 73/61.41 |
| 5,103,181 | 4/1992 | Gaisford et al. | 324/637 |
| 5,192,984 | 3/1993 | Beecher et al. | 356/433 |
| 5,215,715 | 6/1993 | Haswell et al. | 436/175 X |

OTHER PUBLICATIONS

Hinkamp et al., Analytica Chimica Acta, vol. 236, 1990, pp. 345–350: Determination of Total Phosphorous ... Digestion.
Haswell et al., Analyst, vol. 117, Feb. 1992, pp. 117–120: On-line Microwave Digestion ... Elemental Detection.
Chen et al., J. Chem. Soc. Chem. Commun., 1990, pp. 807–809–Preparative Scale Org. Syn. Using Kitchen Microwave Oven.
Burguera et al., Analytica Chimica Acta, vol. 179, pp. 351–357: Flow Injection & Microwave Oven ... and Iron, etc.
Hirai et al., Analytica Chimica Acta, vol. 115, 1980, pp. 269–277: Flow Injection Analysis of Inorganic Polyphosphates.
Aoyagi et al. Analytica Chimica Acta,, vol. 214, 1988, pp. 229–237: Rapid Spectrophotometric ... Including a Capillary Digestor.

Primary Examiner—James C. Housel
Assistant Examiner—Maureen M. Wallenhorst
Attorney, Agent, or Firm—Raymond F. Kramer

[57] ABSTRACT

A process and apparatus for controlled continuous microwave digestion of samples of materials to prepare them for subsequent analyses or other chemical operations. The material to be analyzed, in finely divided form and mixed with digesting liquid, such as a strong acid, is charged as a slug into a flowing liquid carrier stream, usually water, which stream, containing the slug, is passed in a tube through a zone in which the tube and contents are subjected to microwave radiation, to heat the digesting liquid and the material to be digested to promote the digestion. The process and apparatus are modified by inclusion of detecting and controlling steps and corresponding apparatus components to detect a condition of the flowing liquid without physically contacting it, as by determining the dielectric constant of contents of the tube, or a related property of such contents at one or more locations of the tube, usually outside the microwave zone, and controlling operations of the process and apparatus accordingly. Such controlled or controllable operations include charging of subsequent slugs to the system, feeding digested slugs or portions thereof to an autosampler, and backwashing of a filter, and in such operations the controlling device is preferably a microprocessor or computer activated by signals from the detection component and automatically operates appropriate valves, pumps and autosampler. Also within the invention is a procedure for converting a manual process, such as that described to an automatic one.

22 Claims, 4 Drawing Sheets

CONTROL OF CONTINUOUS MICROWAVE DIGESTION PROCESS

This invention relates to a microwave digestion process and to an apparatus for carrying out such a process. More particularly, it relates to controlled continuous digestion of a material, to make it suitable for subsequent analysis or other chemical treatment, by microwave heating a slug of such a material in a digesting liquid, which slug is in a carrier that flows continuously through a tube that is subjected to microwave heating to heat the slug and thereby promote digestion of the material, with the continuous digestion being controlled by a combination of a detection means which detects a property of the flow, such as the dielectric constant or combined equivalent dielectric constant thereof or a property related to such dielectric constant, or a change therein, and generates or modifies a signal related to such detected property without physically contacting the flow, and a controlling means, which controls the process in response to a signal sent to it by the detection means. The invention also relates to a procedure for converting manual microwave digestion processes and apparatuses, such as one in accordance with U.S. Pat. No. 5,215,715 to automatically controlled processes and apparatuses.

In U.S. Pat. No. 5,215,715, there is described a process wherein a material to be digested to make it suitable for chemical analysis thereof is continuously digested in a slug of digesting liquid that is transported in a carrier liquid through a microwave radiation zone in a long thin coiled tube in said zone. The material to be digested is digested in the digesting liquid as such liquid is heated during passage of the slug through the microwave zone. In the apparatus and process described in the patent gas generation during the microwave heating helps to mix the material to be digested, in finely divided form, with the digesting liquid and promotes digestion but before exiting the system after digestion is completed such gas is condensed by the combined actions of a cooler and a backpressure regulator. The liquid resulting is then sent to analysis, which may be effected by an atomic absorption spectrophotometer or other suitable analytical means. The apparatus described in the patent includes mixing means (for mixing the material to be digested, in powder form, with digesting liquid), charging means (to charge a slug of mixed sample and digesting liquid into the carrier stream), backpressure means, filtering means backwashing means and cooling means, with appropriate valves, pumps and lines to effect the desired operations of such means. However, the apparatuses and processes of the patent do not include or utilize any means for automatically controlling the operations of the described system and automatic operation is not taught by the patent (although it is considered to be within the scope of the invention described therein). The invention of the patent is also described by the inventors in an article published in 117 *Analyst* (February, 1992) at pages 117–120. Such patent and article are included herein by reference. The only other prior art known to the present inventors that might be relevant to the instant invention are articles that relate to flow measurement and control by means of capacitance methods and devices. Such articles are at 21 *Water and Waste Treatment* (October, 1978) at pages 55, 57 and 59 and in the second part of a paper entitled *Control and Measurement in Hydraulic Circuits and Equipment* in *PROMOFLUID*, No. 30 (April, 1975) at pages 95–97 (BHRA abstract No. 2.122FP12). Neither of the mentioned prior art abstracts describes nor makes obvious the present invention, which utilizes a capacitor or a plurality of capacitors made up of flowing liquid and non-conductive tubing as the dielectric between conductive "plates" or equivalents to generate a signal which is transmitted to a controller that controls various operations and sequences thereof in a continuous microwave digestion system or process.

In accordance with the present invention a process for controlling a continuous microwave digestion process in which a material to be digested is flowed through tubing in a slug of a digesting liquid which is carried by a carrier liquid, in a continuously flowing stream, which tubing passes through a zone in which it is subjected to microwave radiation to heat the slug to promote digestion of the material by the digesting liquid, comprises detecting a property of a component of such flowing stream, which component may include any gas generated during said heating, at a location of the tubing, without making physical contact with said stream, and controlling a part of the continuous microwave digestion process in a response to said detected property. The invention also relates to an apparatus for carrying out the described process and to a procedure for converting a manual digestion system or process (as of the patent) to one that is automatically controlled.

The invented process (and the corresponding apparatus), which usually utilizes a microprocessor or a computer to control various operations in the process in response to detected flow and the presences of certain components of said flow at certain locations of the tubing, usually external to the microwave zone, allows control of the process so that the presence of the slug of digesting liquid with material to be digested therein is detectable at the end of the digesting operation (usually at the end of the tube) and can be automatically removed then and delivered to an autosampler or to an analytical apparatus or system. By use of the detection apparatus and by selection of an appropriate detection threshold one can direct only a portion of the slug (usually preferably a mid-portion) to the analytical device or to the autosampler, and in that way it is made certain that any carrier liquid is kept out of the material being analyzed. Such carrier liquid, after completion of the digestion, is usually sent to waste, treatment or recovery means. The apparatus can prevent the addition of the next slug to the carrier stream or flow until the earlier slug has passed through the apparatus or it can allow its addition when the earlier slug has passed a point in the process after which such addition of another slug is acceptable and non-interfering. The charging means employed to charge slugs to the carrier in the tube may be kept from charging additional slugs until it is indicated by the detection means that the charging means (which may be a measured volume tube) is clear of any undesirable remains from the previously charged slug. The controlling means may activate the backwashing (normally effected with liquid carrier) apparatus or system in response to passages of a certain number of slugs or in response to the passage of a single slug through the system. Backwashing may be halted and digestion may be resumed automatically when the backwash liquid or liquid passing through the filter after backwashing is free of or essentially free of contaminants from previous charges to the system. Addition of further charges of slugs to the system may be halted until liquid carrier passing through the filter is of desired purity.

The various controlling functions described above are all effected by means of the capacitor-type detector detecting the presence of a component of the flowing stream in the microwave heated tube by determining its dielectric constant or combined equivalent dielectric constant (when the part of the flowing stream contains more than one component). It should be appreciated that the absolute dielectric constant does not have to be measured by the apparatus; it is enough that the property measured be related to the dielectric constant so that the detection means can distinguish between stream components. Such a property is what is meant to be described herein when reference is made to the dielectric constant, combined equivalent dielectric constant or change therein.

The various advantages obtained from the invented processes and apparatuses demonstrate that the invention is more than making a manual process into an automatic process, and devising an apparatus to accomplish that. Because the digesting liquid is usually a strong chemical, such as a strong acid, it is important that the detection means be such that it does not contact the flow, to avoid detrimental reaction of parts of the detection means with the digesting liquid and to avoid contamination of the material being digested. The different dielectric constants or related properties or changes therein that are indicative of the presence in the tubing of carrier liquid, slug or gas allow control of the digesting process precisely and permit inclusion in the apparatus of various means for improving the process, such as means for preventing addition of a second slug until a first slug has cleared the system or has proceeded far enough through the system that the second slug may be added without danger of interference with or contamination by the first slug or any residue thereof left behind (on a filter or on tube walls). Also, such differences allow purgings of charging means, filter means and lines to a point where it is known that they are not contaminated, which improves the digestion process and increases the reliability of analyses run on the digested materials. Other advantages of the invention will be apparent to one of skill in the art from the following description, taken in conjunction with the drawing, in which:

Figure 1:
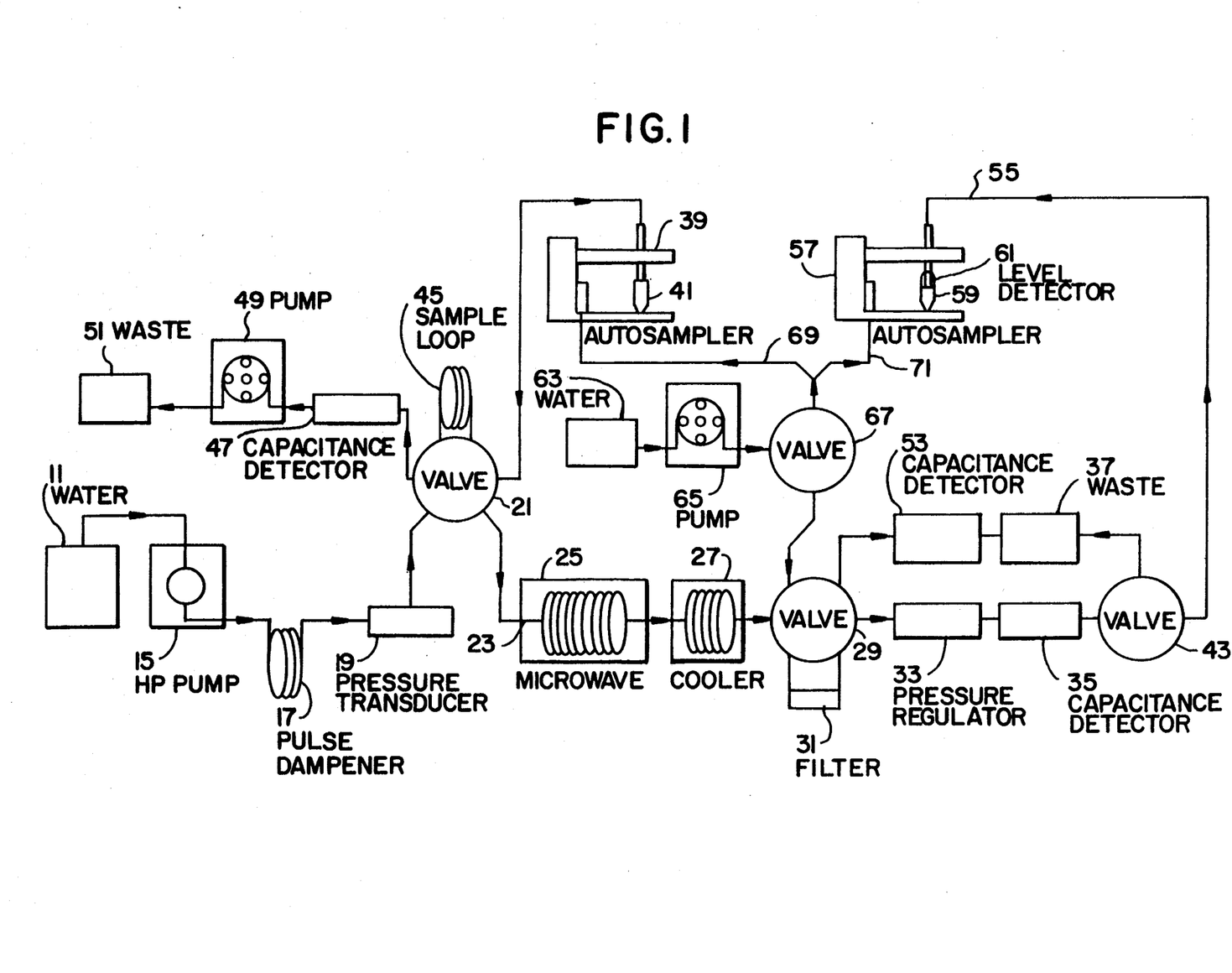
FIG. 1 is a schematic flow diagram of the apparatus of this invention, showing several capacitance detection means in positions thereon.

In FIG. 1 carrier liquid (water) in container 11 or from an equivalent source is delivered to a pump (in this case a high pressure pump) 15 from which it passes through a pulse dampener 17 to a pressure transducer 19 and thence to a multi-way valve 21 which, in a given position, allows the carrier liquid to flow through tubing 23, which is in the form of a coil inside microwave radiation zone or apparatus 25. The carrier liquid passes through a cooler 27 and multi-way valve 29, which directs it through filter 31, after which it passes back through valve 29 to backpressure regulator 33 and capacitance detection means 35 and through valve 43 to waste 37. "Waste" may be used herein to designate "waste, treatment or recovery"). With pure water flowing past the capacitance detector, it is calibrated at an arbitrary count of 200 (counts will be lower for the slug of carrier liquid and material to be digested), which is representative of or related to the dielectric constant of pure water.

To start the digestion process, a mixture of digesting liquid and powdered material to be digested is made (mixer not shown) and is charged to autosampler 39, which includes stirring means, not specifically illustrated, to keep the sample in suspension. From an autosampler tube 41 the mix is delivered to valve 21 which directs it to fill charging means 45, which is a sample loop or coil of measured volume (such as about 10 ml), after which excess mix passes through capacitance detector 47 and is pumped by pump 49 to waste vessel 51 or to treatment or recovery means. Capacitance detection means 47 can be programmed to halt pump 49 when it detects the presence of the mix and such detection means may also be used to detect when the sample loop is clean after being emptied of mix when the mix is charged as a slug to the carrier liquid passing through the system for digestion. Control means may be employed to charge the loop of mix as a slug to the flowing stream of carrier liquid and such means may also be used to prevent the charging of additional mix (for a second slug) to the system until the loop is clean (containing no interfering quantity of mix components from the previous loop contents).

By controlling the positioning of the multi-way valve 29 the filter may be backwashed and capacitance detecting means 53 may be employed to determine when the backwash liquid (normally carrier liquid, which is usually water) is clear of contaminants (reads the calibrated count of 200, the relative capacitance or the dielectric constant measure that is characteristic of pure water), at which point backwashing may be terminated and the controller will allow a further digestion cycle to commence. Alternatively, the capacitance detector 35 may be used to monitor the purity of the carrier liquid after backwashing is halted (after what would usually be considered to be a sufficient backwashing time).

The digested material, in its slug with digesting liquid, after detection by detector 35 is directed by valve 43 through line 55 to autosampling means 57 wherein it fills autosampler container 59. A level detector 61, which may be of a capacitance type, may be installed on the autosampler tubes and may be used to control feeding of the digested material in its digesting liquid to the tubes, but such is not necessary. The controlling means that operates the various components of the system, the valves, pumps, lines, autosamplers, etc., which controlling means will be further described later, may be set so as to feed digested slugs or parts thereof, preferably midportions, to the autosampling means, or may feed substantially all of the slugs to such means.

Both the described autosamplers 39 and 57 are equipped with washing means that clean parts thereof with water. Such means include a source of water 63, a pump 65, a multi-way valve 67 and lines 69 and 71, with means to convey the used wash water to waste. The capacitance detectors (which name is used to cover detectors of capacitance, properties that are related to capacitance, and changes or modifications of such properties) may be so located as to monitor the conditions of liquids in the valves, lines and other auxiliary equipment in the system and to prevent carrying out of the digestion operations until such liquids are in acceptable conditions. However, usually it is enough to monitor the exit portion of the system (such as by using detection means 35).

Figure 2:
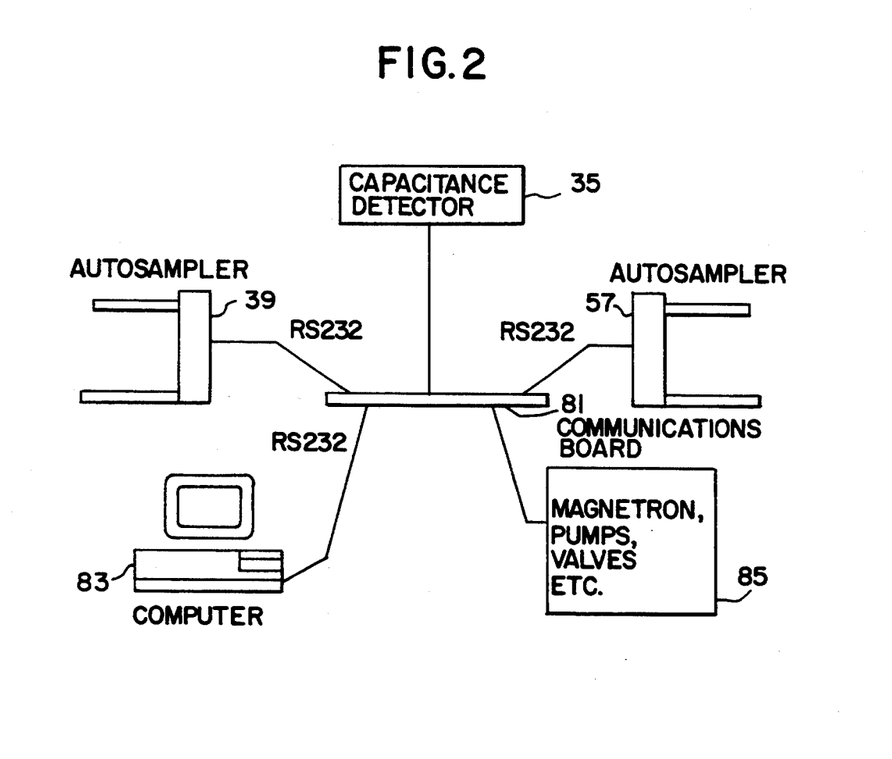
FIG. 2 is a schematic diagram, showing electronics and software control of various components of the apparatus.

In FIG. 2 there is schematically shown a communications board 81 connected to autosamplers 39 and 57, computer 83 and the magnetron, multi-way valves and pumps and any other operable components of the system, represented collectively by numeral 85, by means of RS232 or other communication so that the communications board receives signals from the capacitance detector(s), represented by numeral 35, and by means of a suitable program in the computer (which will not be described in detail because of its length and because it is within the skill of one in the computer art to create it, knowing what is desired), regulates the operation of the digestion system, including the samplings, pumpings, valvings, backwashings, backpressure controls, magnetron controls, cleanings and chargings.

Figure 3:
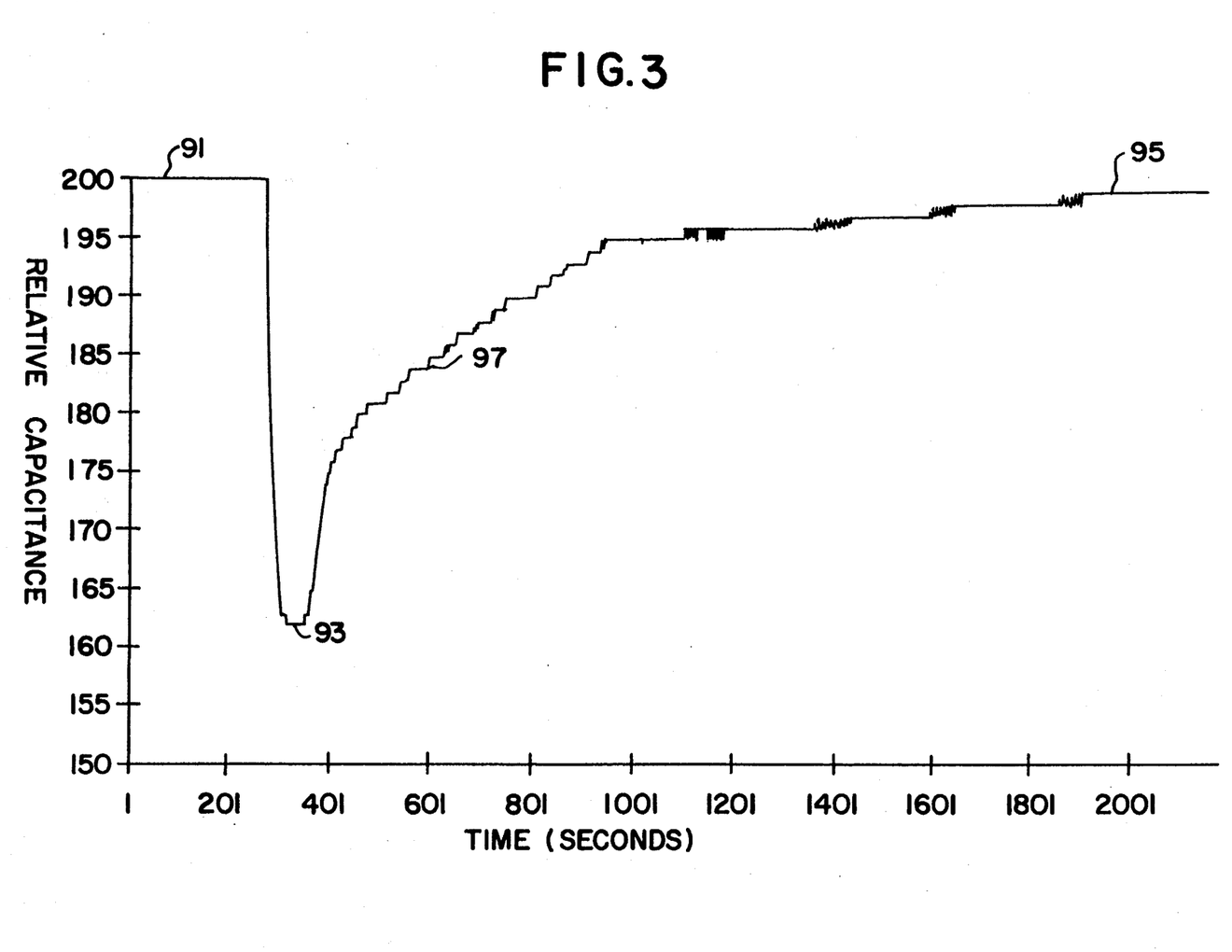
FIG. 3 is a plot of relative capacitance vs. time, as obtained at a capacitance detector located at the end of the digestion process as a slug of material to be digested in digesting liquid is sent through the detector in carrier liquid.

In FIG. 3 a curve of relative capacitance vs. time for the relative capacitance found by detector 35 during An actual digestion is shown. The drop in relative capacitance from 200 at plateau 91 to about 162 indicates that the slug of material to be digested in digesting liquid (which may be digested metal compound in nitric acid) is passing through the capacitance detector during the time between about 300 seconds and 380 seconds after the start of the process, with the "mid-point" passing through the detector at about 330 seconds. Thus, only such sample should be taken to avoid including carrier in it. If it is desired to take even a more central cut of the slug one may, for example, take the cut between 315 and 365 seconds. The flat section of the curve at 95 shows that the stream passing through the tubing at that time is almost pure water (and may be pure enough to allow a subsequent sample to be digested) whereas at 97 such stream still contains an appreciable proportion of slug components.

Figure 4:
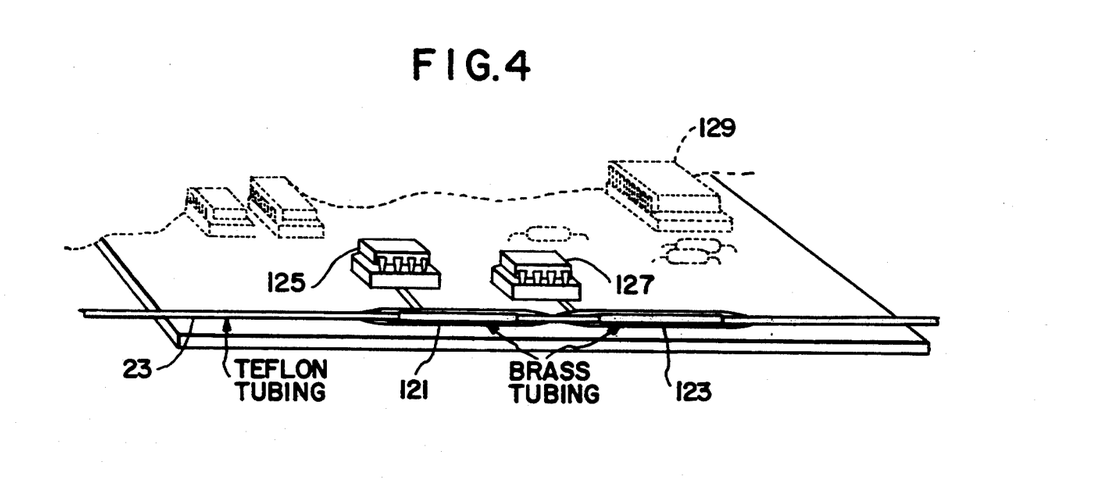
FIG. 4 is a perspective view of a capacitance detection means of the invention and a portion of an integrated circuit board with which it is connected.

In FIG. 4 mounting of capacitance detector components on a circuit board is illustrated. The capacitance detector, as shown, comprises two sections, each of which includes brass or other suitable conductive tubing over tubing of inert plastic, e.g., polytetrafluoroethylene (PTFE or Teflon ®). A useful capacitance detector, as illustrated, is comprised of brass tubes or sheaths 121 and 123, PTFE tubing 23, and flowing liquid inside the PTFE tube (not specifically illustrated), which are shown with oscillator integrated circuit 127, comparator integrated circuit 125 and microcontroller integrated circuit 129.

Figure 5:
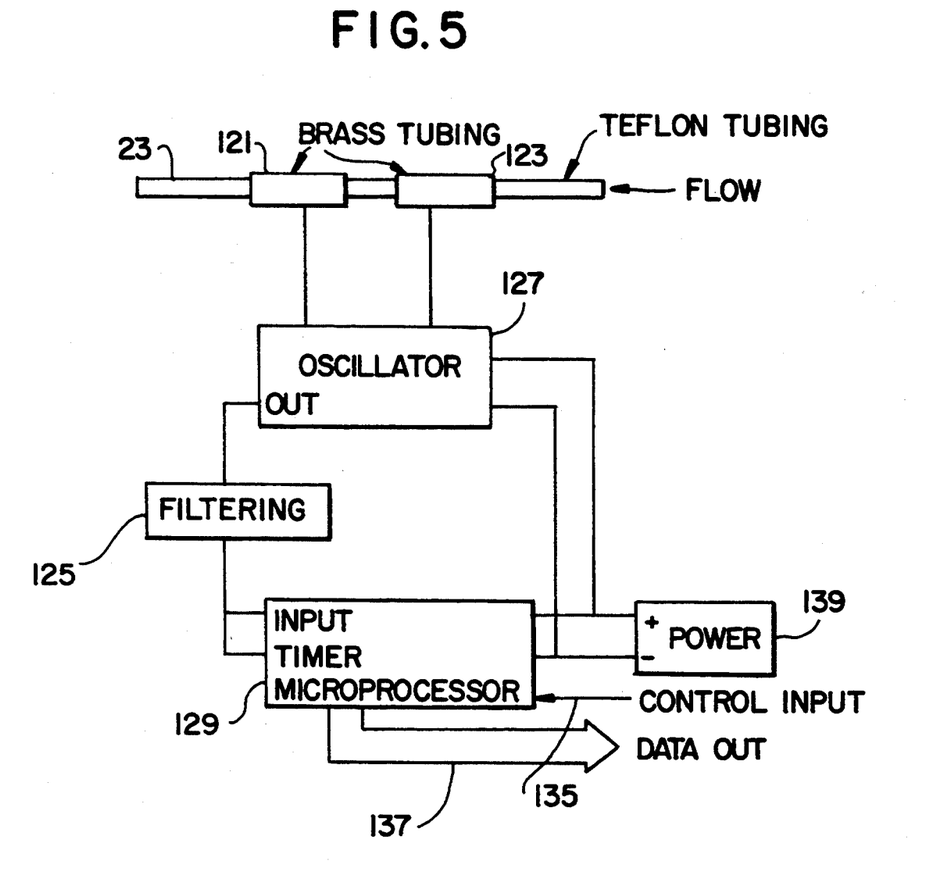
FIG. 5 is a diagrammatic view of the capacitance detection means.

In FIG. 5 the capacitance detection means is illustrated connected to a microprocessor and transmitting data to a controller. The detector comprises Teflon and brass tubes of types previously described, with the brass tubes or separate tube sections 121 and 123 being connected to oscillator 127 (operating at a frequency in the range of 75 to 150 kilohertz) which feeds to a filter 125 and thence to timer and microprocessor 129, to which control input 135 is supplied and from which data out 137 is fed to a computer/controller. Power to the detection means is supplied from source 139 through oscillator 127, which source also supplies power to the microprocessor.

The dielectric constant of the liquid, the capacitance detected by the detection means or a property of the system at the point of the detection means that is related to capacitance, such as wave form, may be utilized by one skilled in the art to operate the various components of the present system so that the process described may be carried out automatically or semiautomatically, as desired. While automatic processes are highly preferred one may utilize the detector of this invention to aid an operator in determining when to collect digested sample, when to start a second digestion, when to halt back-flushing, etc. The various parts of the system are readily obtainable and the assembly thereof is within the skill of one of ordinary skill in these arts (computer electronics and programming). However, some equipment items will be described in some detail for convenience of the reader.

The microwave transmissive tubing is normally a plastic, of a small bore (0.5 to 1.5 mm inside diameter), of which plastics polytetrafluoroethylene (PTFE) has been found to be the best because it is microwave transmissive and inert to many strong digesting acids. However, when other plastics are compatible with the digesting liquid they may also be employed. The tubing for the digesting portion of the system will almost always be PTFE but other plastics may be employed for other parts of the system, such as the lines to waste for the carrier liquid, etc. Brass has been found to be an excellent material for the conductive sheaths of the capacitor but other metals or alloys or other conductors may be substituted for it, such as copper, aluminum, silver and stainless steels. The electronics employed may be essentially the same as those for the CEM MDS (microwave digestion system) 2000 series systems (manufactured by CEM Corporation, Matthews, N.C.). The multi-way valves are preferably either Rheodyne or Lee valves which are resistant to damage by strong acids. The high pressure pump 15 is preferably obtained from Scientific Systems, Inc. and the peristaltic pumps (the remaining pumps) may be from Alieta Corp. (their Model Sl). Autosamplers may be from A. I. Scientific, Inc. (their AIM 1250) and valve motors may be from Burgess Saia, Inc. (Model UFBI). The microwave generator (magnetron) is a 200 watt unit but higher and lower power level magnetrons may be utilized, depending on the sizes of the slugs being heated and on the carrier:slug ratios employed. Pressure regulators that are employed will usually be capable of regulating pressure within the 50 to 200 lbs./sq. in. range and will be adjustable. A suitable such regulator is made by Upchurch Corp. The computer employed is an IBM compatible 386SX 16 Mhz but any comparable one is acceptable. The program is written in computer language C for execution under the operating system MS DOS, In addition to the parts described in the description of the drawing, there may be included in the described system safety shut-down mechanisms and appropriate electronics to prevent secondary damage in the event of a component failure. Specific such safety systems are preferably employed for at least the high pressure pump, autosampler(s) and microwave generator but they are also desirably employed at various other locations in the apparatus that are subject to possible failure in use, and especially in those locations where contact is made with the digesting liquid.

In the present invention the means for detecting the presence of particular substances at certain locations of the tubing is a capacitor that includes as an element thereof the flowing fluid in the tubing. The presence of a different fluid, which is of a different dielectric constant, changes the capacitance of the capacitor and that change or a change in a related property is determinable and can be used to control operation of the digestion system. In the illustrated embodiment of the invention the capacitor is connected as a frequency determining element in an electronic oscillator and produces different wave forms with different periods. For example, air results in a period of 8.7 microseconds, water 9.4 and acid solution 12.4 microseconds. Such differences are readily distinguishable and information related to such a change when a selected one of such materials is found to be present in the capacitor is sent to the controller from the detector and can cause the controller to act. In the described systems stray capacitance and lead capacitance should be minimized to ensure maximum frequency variations with dielectric changes. Also, the dielectric constant of the plastic tubing should be low compared to those of the fluids for that same reason. A calibration command input is provided in the system so that a reference time period is measurable while the calibration liquid (the carrier) is in the system. All other measurements of a capacitance-related property are relative to such calibration measurement. The period of the oscillator is measurable by a microcontroller or similar circuitry and fluctuations in periods are determinable as the dielectric constants of the fluids and of the capacitors (of which they are components) vary.

In the previous description of the system of this invention the apparatus and its components were described, as well as the operation thereof. In addition to the invented apparatus and process, also within the invention is a procedure for converting a "manual" digesting apparatus of the type of U.S. Pat. No. 5,215,715 to an automatic one. That can be accomplished by installing in such apparatus detection means for detecting a property of a material and for generating or modifying a signal (usually electrical) in response to said detected property, a computer, microprocessor or similar controlling means for controlling operations of the various components of said apparatus, and means for communicating said signal or modified signal with said controlling means. The modification procedure is also applicable to improving various other manual chemical processes to make them automatic.

The following is a description of steps that are taken when the apparatus is employed to digest a sample for subsequent analysis or chemical reaction. Apparatus references are to FIG. 1.

1. The sample or group of samples is prepared for digestion, often by mixing of a powdered sample with digesting acid.
2. The sample to be digested, in the digesting liquid, is placed in an autosampler cup, or a plurality of samples is placed in such cups.
3. The sample cup(s) is/are placed on the uptake tray of the autosampler.
4. A digestion sequence (program) is selected for digesting the sample (the sequence being from a number of such established sequences that have been found applicable).
5. Empty sample cups are placed on the collection autosampler.
6. The system is turned on and pure water (preferably distilled and/or deionized) is pumped through the tubing, taking the following path:
   a. pure water reservoir or source to high pressure pump 15 (see FIG. 1),
   b. through pulse dampener 17,
   c. through pressure transducer 19,
   d. through valve 21,
   e. through the microwave zone 25,
   f. through cooler 27,
   g. through valve 29,
   h. through filter 31,
   i. through valve 29,
   j. through backpressure regulator 33,
   k. through exit capacitance detector 35,
   l. through valve 43, and
   m. to waste 37,
6A. Simultaneously pure water is flushed through the sample charging flow path:
   a. pure water source 63 to pump 65,
   b. through valve 67,
   c. through tubing 69,
   d. through autosampler 39,
   e. through valve 21,
   f. through sample loop 45,
   g. through capacitance detector 47,
   h. through pump 49, and
   i. to waste 51.
7. The START button is pressed to begin the sequence. Such command resets all system functions.
8. The system is now filled with pure water. The reset command sends a calibration signal to each of the three capacitance detectors, which are now calibrated on pure water at an arbitrary count of 200.
9. The system is now ready for taking its first sample for digestion.
10. The uptake autosampler 39 moves its probe to position over the first sample for digestion and lowers the probe to the bottom of the sample cup. The stirrer on the uptake sample probe is turned on.
12. A delay time is set to allow the stirrer to mix the sample thoroughly in the sample cup (typically such time is 5 to 10 seconds).
13. After the delay the sample uptake pump 49 is activated, which draws the sample through valve 21, charging means (loop or coil) 45 and detector 47 and sends some of the sample to waste 51 unless pump 49 is halted in response to a signal generated by detector 47.
14. The pump 49 will continue pumping until capacitance detector 47 detects a change in capacitance value that brings it to the relative capacitance of the sample (about 165 for a nitric acid digesting liquid), which is distinguishable by the detector from the relative capacitance of water (or gas, such as air). It should be noted that the relative capacitance for the digesting liquid is known in advance and depends to some extent on the type of digesting liquid being employed. The computer program takes such differences into account.
15. When the capacitance detector 47 detects the presence of the sample to be digested the controller computer issues a command for valve 21 to index so that the contents of the sample loop are sent as a slug into the flowing stream of carrier liquid (normally water).

16. The carrier liquid, carrying the slug of sample, flows into the microwave zone or chamber 25 through the thin microwave transmissive tubing. The carrier absorbs microwave energy and is heated in the chamber because it is polar in nature but the slug of sample absorbs more microwave energy and is heated more because it is more polar. During passage through the microwave chamber the heated slug gives off gases, such as NO, $NO_2$ and $CO_2$, and bubbles, thereby helping to mix the components thereof and promoting digestion as new surfaces of material to be digested and digesting liquid are brought into contact. Such bubbling is desirably controlled for the sample being heated, so that the slug remains intact in the carrier liquid (although it becomes lengthened).

17. The flow then reaches the cooler 27, which cools it sufficiently to condense gases that are in the slug, so that under the pressure of the system the slug is in liquid state, without the presence therein of gas sufficient to cause detection of a false capacitance.

18. After cooling, the flow (including the slug) passes through valve 29 and filter 31 wherein any insolubles present are removed. At this point all the digestable material has been digested and is in soluble form in the digesting liquid.

19. The cooled and filtered flow then passes through a different passageway in valve 29 to pressure regulator 33 which had been set for an appropriate pressure so as to maintain a backpressure on the system sufficient to keep the cooled slug in liquid form.

20. The flow next enters the exit capacitance detector 35, which had been calibrated to 200, as in step 8.

21. After action described in step 15, the injection of the sample into the stream of carrier liquid, the controller computer instructs autosampler 39 to return its probe to the wash station on the autosampler, where pure water is pumped through the autosampler tubing to clean it.

22. After the injection of the sample into the liquid carrier stream, as described in step 15, the computer causes the system to wait until the presence of the slug is detected by the exit capacitance detector. The computer is continually monitoring the signal from capacitance detector 35 and is programmed to take action when the signal from the detector is at a pre-set value that is indicative of the presence of the slug or a desired portion thereof (often the middle portion).

23. Upon the signal from capacitance detector 35 indicating the presence of the slug at such detector, the computer activates valve 43 to direct the slug to collection autosampler 57 (previously the stream or flow of material [carrier liquid] had been proceeding to waste vessel or line 37).

24. Before receiving the slug of digested material in digesting liquid the collection probe of autosampler 57 is continually washed with water to keep it free of contamination.

25. As the slug is detected by the exit capacitance detector 35 the controller computer causes the collection probe of autosampler 57 to be raised and positioned over a waste section of the autosampler.

26. A time interval is set by the computer to allow sufficient purging of water from the probe so that it is filled with undiluted digested material in digesting liquid.

27. Valve 43 is switched momentarily to waste position while the sample probe of the autosampler 57 is moved to a specified height in a collection cup of the autosampler.

28. Valve 43 is repositioned to allow digested sample or slug material to fill an autosampler collection cup.

29. The collection probe of autosampler 57 is returned to position over the waste location of the autosampler wash station and valve 43 is set to send carrier liquid (water) to the autosampler, which cleans the autosampler collection probe and the tubing between valve 43 and the autosampler.

The above description describes a complete process and apparatus for digesting a sample of material, which may be an ore, waste water, industrial waste, radioactive waste, food, oil, milk, solids, coal, animal product, vegetable product or any other material to be analyzed or chemically reacted after digestion. Additional operations are primarily to ensure that the equipment utilized is made fit for use with other samples of such materials, which may be digested in the same type of digesting liquid or different ones, and which may utilize the same or different carrier(s).

30. To clean filter 31 valves 29 and 67 are automatically set in response to computer command so that passage of flow through the main system is suspended and pure water is sent from source 63 via peristaltic pump 65 to backwash filter 31. When detector 53 indicates that only pure water is flowing past it (to waste 37), the backwashing may be terminated by the computer and the filter is ready for use again. To double check on the cleanliness of the filter, after the backwash liquid is found to be clean, water may be flowed through the filter in normal flow direction and its purity may be checked by detector 35 or detector 53. If either detector signal indicates that the filter water is not up to standard the computer automatically resumes backwashing (and during such backwashing the system is otherwise immobilized).

31. The sample loop or charging means 45 is cleaned in a manner similar to that described above for cleaning the autosampler and for testing the purity of the flow through the filter after backflushing thereof. Sample loop 45 has pure water pumped through it from source 63 by pump 65 through valve 67 and through line 69 to the wash reservoir on autosampler 39, the water is drawn through valve 21, loop 45 and detector 47 out through pump 49 to waste 51 (or treatment or recovery means). The detector 47, which includes a microcontroller or a similar circuit, converts the signal to a number that is sent to the computer controller when the relative capacitance (about 200 for water) indicates the presence of pure water (or other carrier) and then the computer permits the charging to the charging means 45 and to the system of another slug of material to be digested in digesting liquid, providing that other parts of the system are satisfactorily clean, too.

32. In similar manner the exit capacitance detector 35 monitors the purity of the system when pure water is flowed through the system. When the detector 35 indicates that the carrier (water) is pure the computer will permit the various components of the system to operate, which operations otherwise would be prevented by the computer.

The system, the operation of which has been described in detail above, is an automatic one which has been proven in repeated experiments to produce excellent digestions that are replicatable. The various checks on operation of the system have been described but it is clear that additional such checks may be installed in the system and some may be omitted under certain circumstances. At the heart of the system is the employment of a capacitor or capacitors in which the flowing liquid passing through the system is a part of the dielectric of the capacitor along with the plastic or other non-conductive tubing in which the digestion takes place. The system takes advantage of the fact that a change in the dielectric constant of the liquid or other fluid flowing through the "capacitor" causes a change in the capacitor's characteristics and output and such output can be evaluated by a controller (which may be a computer) which controls the system accordingly and similarly controls the process.

The following example and data are given to show that the invented system, including apparatus and process, is a valid one that yields satisfactorily consistent results, comparable to results obtained by employing "standard" digestion procedures.

Utilizing a continuous digesting system essentially like that illustrated in FIG. 1 and described in this specification, but with an end capacitance detector only being employed, ten samples of wastewater were digested in about 10% aqueous nitric acid, with the volume of the slug charged in the charging loop being ten ml in each case and with the times of each run being about ten minutes. After completions of the digestions the samples were analyzed for aluminum, boron, barium, calcium, cadmium, cobalt, chromium, copper, iron, potassium, lithium, magnesium, manganese, molybdenum, sodium, nickel, phosphorus, lead, sulfur, antimony, silicon, strontium, titanium, thallium, vanadium, zinc and zirconium by spectrophotometric means or other suitable analytical equipment. The averages of the amounts present and the standard deviations were as follows:

| Element | Value |
|---|---|
| Aluminum | 0.378 ppm ± 0.034 ppm |
| Boron | 0.130 ppm ± 0.010 ppm |
| Barium | 0.018 ppm ± 0.026 ppm |
| Calcium | 38.660 ppm ± 2.833 ppm |
| Cadmium | 0.000 ppm ± 0.000 ppm |
| Cobalt | 0.010 ppm ± 0.005 ppm |
| Chromium | 0.045 ppm ± 0.005 ppm |
| Copper | 1.013 ppm ± 0.149 ppm |
| Iron | 41.219 ppm ± 5.058 ppm |
| Potassium | 2.507 ppm ± 0.222 ppm |
| Lithium | 0.095 ppm ± 0.004 ppm |
| Magnesium | 23.388 ppm ± 1.784 ppm |
| Manganese | 0.344 ppm ± 0.037 ppm |
| Molybdenum | 15.555 ppm ± 1.261 ppm |
| Sodium | 102.004 ppm ± 8.269 ppm |
| Nickel | 0.015 ppm ± 0.004 ppm |
| Phosphorus | 0.132 ppm ± 0.206 ppm |
| Lead | 0.097 ppm ± 0.020 ppm |
| Sulfur | 19.086 ppm ± 1.549 ppm |
| Antimony | 0.058 ppm ± 0.029 ppm |
| Silicon | 2.357 ppm ± 0.176 ppm |
| Strontium | 0.308 ppm ± 0.023 ppm |
| Titanium | 0.007 ppm ± 0.001 ppm |
| Thallium | 0.035 ppm ± 0.049 ppm |
| Vanadium | 0.015 ppm ± 0.002 ppm |
| Zinc | 0.160 ppm ± 0.088 ppm |
| Zirconium | 0.014 ppm ± 0.002 ppm |

Although some of the results of the analyses have standard deviations greater than desirable, on the whole the results are satisfactorily consistent for the microsamples employed and are comparable to results that would be obtained by conventional digestion analysis processes. Therefore, it is considered that the digestions were successful. When the additional capacitance detectors and controlling mechanisms described in this specification are included in the system employed, it is expected that the results obtained will be even better.

In other analyses samples were analyzed after both the experimental and control digestions. Such analyses were for iron, sulfur, calcium and copper and the results reported are the means for ten determinations each. For the iron analysis tile control digestion analyzed 7.982 parts per million whereas the experimental (continuous automatic) digestion analyzed 8.227 ppm, a difference of 3.07%. For the sulfur analysis the figures were 293.14 for the control and 294.42 for the experimental, a difference of 0.44%. For the calcium analysis the control digestion analyzed 38.56 ppm while the experimental digestion analyzed 39.03 ppm and for the copper analysis the control digestion analyzed 1.001 ppm and the experimental analyzed 0.995 ppm. The difference between such experimentals and such controls were 1.22% and 1.61%, respectively. Such small variations from the results of an accepted process are considered acceptable.

The various advantages of the present system, apparatus and process have been alluded to before in this specification but some will be additionally detailed here. Accurate and controllable digestions are obtainable without the need for much human intervention, except to fill a charging autosampler and press a start button. The system is capable of digesting different materials in different digesting liquids, and the power, flow rate, cuts of the slugs for analyses, pressure and feeds to the autosampler immediately before the analytical means that are employed in conjunction with the system all may be varied, depending on the program in the computer. Thus, the system is exceedingly versatile. The system is also self-cleaning and self-regulating, with feeds being prevented when the system is not ready for them. Our previous methods for controlling the operation of continuous digestion processes, like that of U.S. Pat. No. 5,215,715, were based on charging the sample to be digested and the carrier to the system at a known rate, which would theoretically allow one to determine how long the material would be in the microwave zone and how much microwave radiation it could be expected to absorb. However, gas emission during heating can change flow rates dramatically and therefore control of the system sometimes should not rely exclusively on flow rate timing. For effective digestion (system performance) it is desirable to incorporate monitoring devices to locate the sample slug in the flow path with respect to the active components (valves, pumps, etc.). The filtering, backwashing and cleaning features of the invention help to prevent any clogging of the thin tubing. Furthermore, the system readily lends itself to additional modifications to permit further controlling of the digestion process carried out within it.

The invention has been described with respect to illustrations and examples thereof but is not to be limited to these because one of skill in the art, with the present specification and drawing before him/her will be able to make substitutions therein and utilize equivalents without departing from the scope of the invention.

What is claimed is:

1. A process for controlling a continuous microwave digestion process in which a first material to be digested is flowed through tubing in a slug of first digesting liquid, which slug is carried through the tubing by a carrier liquid, in a continuously flowing stream, which tubing passes through a zone in which the slug, containing the first material to be digested, is subjected to microwave radiation to heat the slug to promote digestion of the first material by the first digesting liquid which controlling process comprises noninvasively detecting a property selected from the group consisting of a dielectric constant of the slug, a combined equivalent dielectric constant of the slug, a change in dielectric constant of the slug relative to the carrier liquid, and a change in the combined equivalent dielectric constant of the slug relative to the carrier liquid, at a location near a point at which the slug exits from the zone in which the slug is subjected to microwave radiation, and removing the slug of first digested material in first digestion liquid from the carrier liquid and the tubing in response to the detected property of the slug.

2. A process according to claim 1 wherein the property detected is a change in dielectric constant of the slug relative to the carrier liquid or a change in the combined equivalent dielectric constant of the slug relative to the carrier liquid, and when the detected property indicates the presence of the slug of digested first material in digesting liquid at said location, said slug is removed and is analyzed or sent to collecting means.

3. A process according to claim 1 wherein the detected property is continuously and automatically determined and when said determining indicates the presence of the slug at said location, said slug or a portion thereof is automatically sent to autosampling means for subsequent analysis.

4. A process according to claim 3 wherein when the detected property indicates that the slug has passed said location, so that the flowing stream is essentially pure carrier liquid, said carrier liquid is automatically sent to waste or to treatment or recovery means.

5. A process according to claim 4 wherein when the detected property indicates that the flowing stream is essentially pure carrier liquid which does not contain any significant proportion of said first digested material and said first digesting liquid after passage through the tubing, a second material to be digested, in a second digesting liquid, is automatically charged to the tubing and forms a second slug of material to be digested, and wherein said second material is digested, one of said detected properties of the second slug is determined at a location near a point at which the second slug exits from the microwave radiation zone and a longitudinally middle portion of said second slug is automatically charged to autosampling means for analysis.

6. A process according to claim 5 wherein the first material to be digested, in said first digesting liquid, is charged as a first slug to a stream of carrier liquid through a charging means that is subsequently employed to charge the second material to be digested, in a second digesting liquid, as a second slug, to the carrier liquid, and wherein one of said detected properties of the carrier liquid, which flows through the charging means, is determined after charging of the first slug to the stream of carrier liquid to determine when the carrier liquid contains no significant proportion of said first material to be digested, after which the second slug is charged to the carrier liquid through the charging means.

7. A process according to claim 6 wherein after microwave heating of said first slug of material to be digested in said first digesting liquid, during which heating, gas is generated, the flowing stream, which includes gas bubbles, is cooled and is filtered through a filter to remove any insoluble material, and after filtration and completion of the digestion, the filter is backwashed with backwash liquid and one of such detected properties of the backwash liquid is determined after said backwash liquid passes backward through the filter, and feeding of said second slug of material to be digested in said second digesting liquid to the carrier stream is delayed until the detected property of the backwash liquid indicates that the backwash liquid does not contain any significant proportion of said first material that had been charged to the flowing stream as a slug in the first digesting liquid.

8. A process according to claim 7 in which the flowing stream is pumped by pumping means through valves and after digestion, the first digested material in the first digesting liquid is autosampled by autosampling means, wherein said pumping and autosampling are automatically carried out by sending control signals corresponding to the detected properties for both the backwash liquid and the carrier liquid to a computer or other controlling means, and wherein said pumping and autosamplings are controlled by means of said signals.

9. A process according to claim 8 wherein the first and second materials to be digested are water insoluble metal compounds, the first and second digesting liquids are the same strong acid or an aqueous solution thereof, and the carrier liquid is water.

10. A process according to claim 1 wherein the first material to be digested is a water insoluble metal compound, the first digesting liquid is a strong acid or aqueous solution thereof and the carrier liquid is water.

11. A process according to claim 1 wherein flowing of the first material to be digested, the first digesting liquid and the carrier liquid through the tubing is automatically controlled by sending control signals corresponding to the detected property to a computer, microprocessor or other controller and controlling said flowing of said first material, digesting liquid and carrier liquid in response to said control signals.

12. An apparatus for controlling a continuous flow microwave digestion process in which a material to be digested is flowed through a tube in a slug of digesting liquid, which slug is carried by a carrier liquid in a continuous flowing stream, which comprises a microwave radiation zone, a tube in said zone, means for passing a slug of material to be digested, in a slug of digesting liquid through said tube in said zone to heat the slug and to promote digestion of said material by said digesting liquid, noninvasive detection means, which detects a property selected from the group consisting of a dielectric constant of the slug, a combined equivalent dielectric constant of the slug, a change in the dielectric constant of the slug relative to the carrier liquid, and a change in the combined equivalent dielectric constant of the slug relative to the carrier liquid, at a location near a point at which the tube exits from the microwave radiation zone, means for removing the slug of digested material in digesting liquid from the carrier liquid and the tubing in response to the detected property of the slug, and means for controlling the continuous flow microwave digestion process in response to said detected property.

13. An apparatus according to claim 12 wherein the microwave radiation zone is a chamber, the tube is microwave transmissive and the detection means signals the controlling means when a slug of digested material is at a location near a point at which the tube exits from the chamber.

14. An apparatus according to claim 13 wherein the means for passing the contents through the tube is a pump, and the removing means is one which is capable of automatically controlling a means for sending said slug or a portion thereof to analytical or collecting means.

15. An apparatus according to claim 14 which further comprises backwashing detection means located so as to be capable of detecting dielectric constant, combined equivalent dielectric constant or change therein of backwashing carrier liquid, and control means responsive to said backwashing detection means, to terminate backwashing when the backwashing carrier liquid is essentially pure carrier liquid.

16. An apparatus according to claim 14 which further comprises an autosampler located downstream of the chamber for collecting samples digested materials in digesting liquid and for feeding such to analytical means, wherein the detection means is capable of determining the presence of longitudinally middle portions of the slugs, and wherein the controlling means allows feeding of such middle portions of said slugs to the autosampler for subsequent analysis in response to a control signal from the detection means.

17. An apparatus according to claim 14 which further comprises charging means for charging first and second slugs of materials to be digested, in digesting liquids, into the carrier liquid in the tube where the tube enters the chamber, and wherein said controlling means allows feeding of the second slug to the tube only after the detection means indicates that the first slug has passed through the tube.

18. An apparatus according to claim 17 wherein the charging means includes tubing that is connected with the tubing in the chamber, through which charging means tubing carrier liquid is feedable to the tubing in the chamber, and which charging means comprises additional second detection means for determining dielectric constant, combined equivalent dielectric constant or change of the carrier liquid, said second detection means is located at the charging means tubing and is capable of determining when carrier liquid passing through the charging means tubing is free of or essentially free of material to be digested and digesting liquid, and means outside the chamber for preventing charging of any subsequent material to be digested, in digesting liquid, when the carrier liquid is not free of or is not essentially free of said material to be digested and said digesting liquid.

19. An apparatus according to claim 12 wherein the controlling means is a computer or microprocessor and the apparatus comprises means for communicating said detected property from the detection means to the computer or microprocessor via a control signal.

20. An apparatus according to claim 12 wherein the detection means comprises a capacitor of electrically non-conductive, microwave transmissive tubing, flowing stream contents of said tubing and a pair of separated electrically conductive sheaths about said tubing, with alternating current connected to the conductive sheaths.

21. An apparatus according to claim 20 wherein said detection means comprises polytetrafluoroethylene tubing, flowing water containing slugs of metallic compounds in strong acid in said tubing, and brass sheaths about the tubing at a location of the detection means, with the alternating current being of a frequency in the range of 75 to 150 kilohertz.

22. A process for automatically controlling an apparatus for carrying out a continuous flow microwave-digestion process, in which digestion process a material to be digested is flowed through tubing in a slug of digesting liquid, which slug is carried by a carrier liquid, which tubing passes through a zone in which the tubing is subjected to microwave radiation to heat the contained slug and promote digestion of the material by the digesting liquid, which apparatus includes a source of microwave radiation, a zone into which said microwave radiation is directed, tubing for transporting the carrier liquid and contained slug through said zone, pumping means for pumping the carrier liquid and contained slug through the tubing, valving means for regulating flow of the carrier liquid and contained slug through the apparatus, sample charging means for charging material to be digested, in digesting liquid, to the carrier liquid, wherein the material to be digested is passed as a slug through the microwave zone in the tubing, autosampling means for transferring digested material in a slug of digesting liquid to analytical means, filter means for removing insoluble materials from the carrier liquid and contained slug, cooling means for cooling the carrier liquid and contained slug and for condensing excess gas in the slug, backpressure controlling means to condense said excess gas in the slug, and means for removing the slug of digested material in digesting liquid from the carrier liquid and the tubing in response to a detected property of said slug at a location near a point at which the tube exits from the microwave radiation zone, wherein said controlling process comprises installing in said apparatus detection means for detecting a property of a slug of material in a digesting liquid in a carrier liquid in said tubing without contacting said slug, wherein said property is selected from the group consisting of a dielectric constant of the slug, a combined equivalent dielectric constant of the slug, a change in dielectric constant of the slug relative to the carrier liquid, and a change in the combined equivalent dielectric constant of the slug relative to the carrier liquid means for generating or modifying a signal in response to said detected property, control means which is a computer, microprocessor or similar control means which can control operation of the pumping means, valving means, autosampling means, sample charging means, filter means, backpressure controlling means, cooling means and removing means during the continuous flow microwave digestion process, and means for transmitting said signal modified signal to said control means.

* * * * *